United States Patent [19]
Byrd

[11] Patent Number: 5,638,814
[45] Date of Patent: *Jun. 17, 1997

[54] ENDOTRACHEAL TUBE HOLDING DEVICE AND ASSOCIATED TUBE HOLDING METHOD

[76] Inventor: Timothy N. Byrd, P.O. Box 490, Townsend, Tenn. 37882

[*] Notice: The term of this patent shall not extend beyond the expiration date of Pat. No. 5,448,985.

[21] Appl. No.: 516,817

[22] Filed: Aug. 18, 1995

Related U.S. Application Data

[63] Continuation-in-part of Ser. No. 328,685, Oct. 25, 1994, Pat. No. 5,448,985.

[51] Int. Cl.⁶ .................................................. A61M 16/00
[52] U.S. Cl. ............................ 128/207.17; 128/DIG. 26; 128/DIG. 15
[58] Field of Search ....................... 128/207.17, DIG. 24, 128/DIG. 15

[56] References Cited

U.S. PATENT DOCUMENTS

| | | | |
|---|---|---|---|
| D. 310,721 | 9/1990 | Beisang | D24/49 |
| 3,046,989 | 7/1962 | Hill | 128/348 |
| 3,826,254 | 7/1974 | Mellor | 128/133 |
| 3,927,676 | 12/1975 | Schultz | 128/351 |
| 3,977,407 | 8/1976 | Coleman et al. | 128/348 |
| 4,120,304 | 10/1978 | Moor | 128/348 |
| 4,142,527 | 3/1979 | Garcia | 128/348 |
| 4,249,529 | 2/1981 | Nestor et al. | 128/207.17 |
| 4,327,716 | 5/1982 | Ansted | 128/133 |
| 4,333,468 | 6/1982 | Geist | 128/133 |
| 4,351,331 | 9/1982 | Gereg | 128/207.17 |
| 4,489,723 | 12/1984 | Simons et al. | 128/207.16 |
| 4,569,348 | 2/1986 | Hasslinger | 604/179 |
| 4,583,976 | 4/1986 | Ferguson | 604/174 |
| 4,671,787 | 6/1987 | Widman | 604/179 |
| 4,690,675 | 9/1987 | Katz | 604/177 |
| 4,744,358 | 5/1988 | McGinnis | 128/207.17 |
| 4,774,944 | 10/1988 | Mischinski | 128/207.17 |
| 4,799,923 | 1/1989 | Campbell | 604/179 |
| 4,822,342 | 4/1989 | Brawner | 604/180 |
| 4,823,789 | 4/1989 | Beisang | 128/207.18 |
| 4,836,200 | 6/1989 | Clark | 128/207.18 |
| 4,932,943 | 6/1990 | Nowak | 604/180 |
| 5,009,227 | 4/1991 | Nieuwstad | 128/207.17 |
| 5,037,397 | 8/1991 | Kalt et al. | 604/174 |
| 5,038,778 | 8/1991 | Lott | 128/207.17 |
| 5,042,477 | 8/1991 | Lewis | 128/207.17 |
| 5,135,506 | 8/1992 | Gentelia et al. | 605/180 |
| 5,163,914 | 11/1992 | Abel | 604/180 |
| 5,215,532 | 6/1993 | Atkinson | 604/180 |
| 5,306,233 | 4/1994 | Glover | 602/41 |
| 5,448,985 | 9/1995 | Byrd | 128/207.17 |

*Primary Examiner*—Aaron J. Lewis
*Attorney, Agent, or Firm*—Pitts & Brittian, P.C.

[57] ABSTRACT

An endotracheal tube holding device for securing the position of an endotracheal tube. The tube holding device (10) includes first and second tube engaging apparatus (14, 16), each of which includes a foundation strap (24) having an outer bonding surface (30) proximate its distal end portion (26). Each of the tube engaging apparatus (14, 16) also includes a tube engaging strap (36) for releasably engaging and securing the position of the endotracheal tube (12). The tube engaging straps (36) each define a proximal end (38) secured to the operatively associated foundation strap (24) and an inner surface (42) coated with an adhesive for releasably engaging the outer bonding surface (30) of the operatively associated foundation strap (24). Also provided is a securing strap (18) having a first end portion for releasably engaging the proximal end portion of the foundation strap (24) of the first tube engaging apparatus (14) and a second end portion for releasably engaging the proximal end portion of the foundation strap (24) of the second tube engaging apparatus (16).

20 Claims, 11 Drawing Sheets

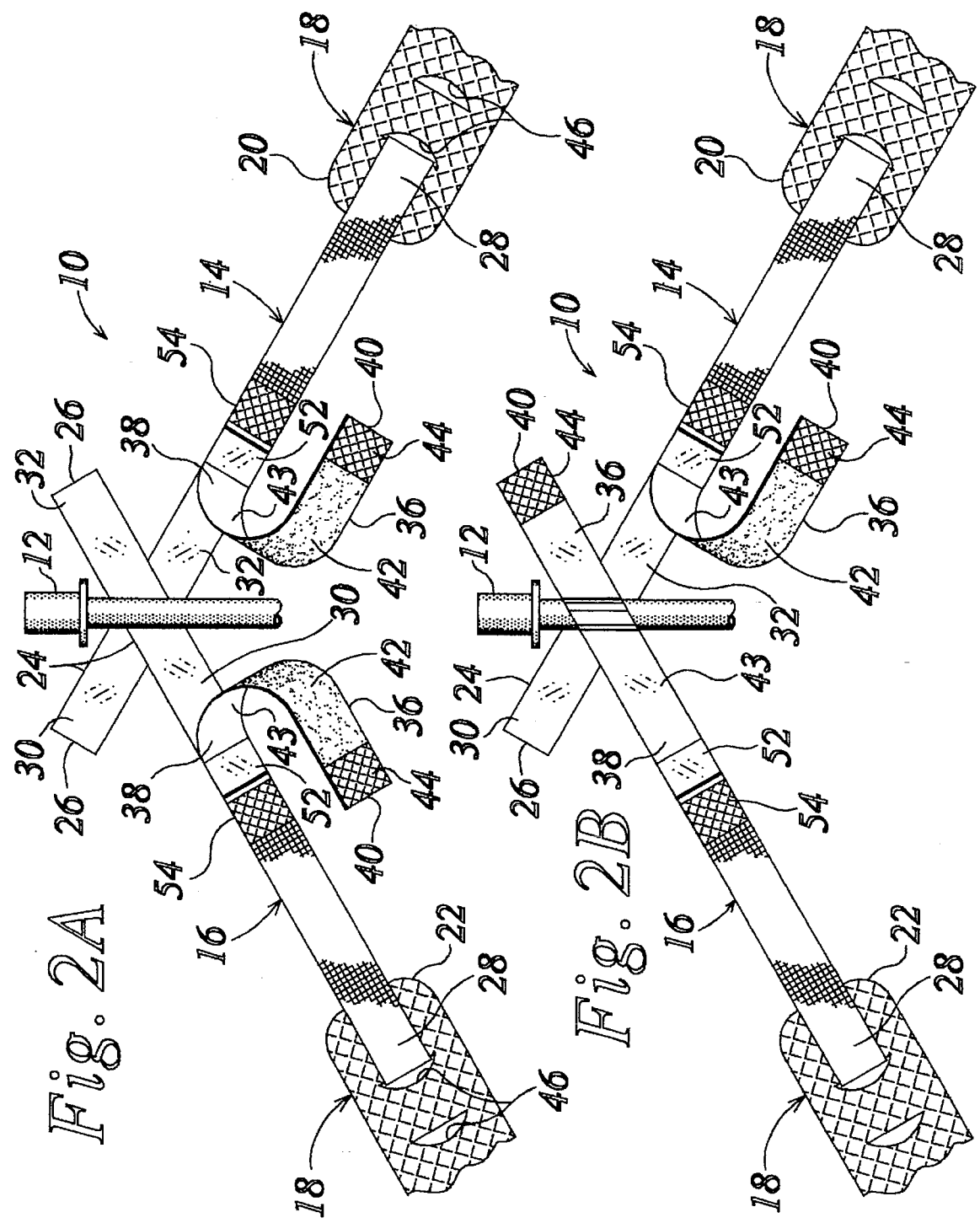

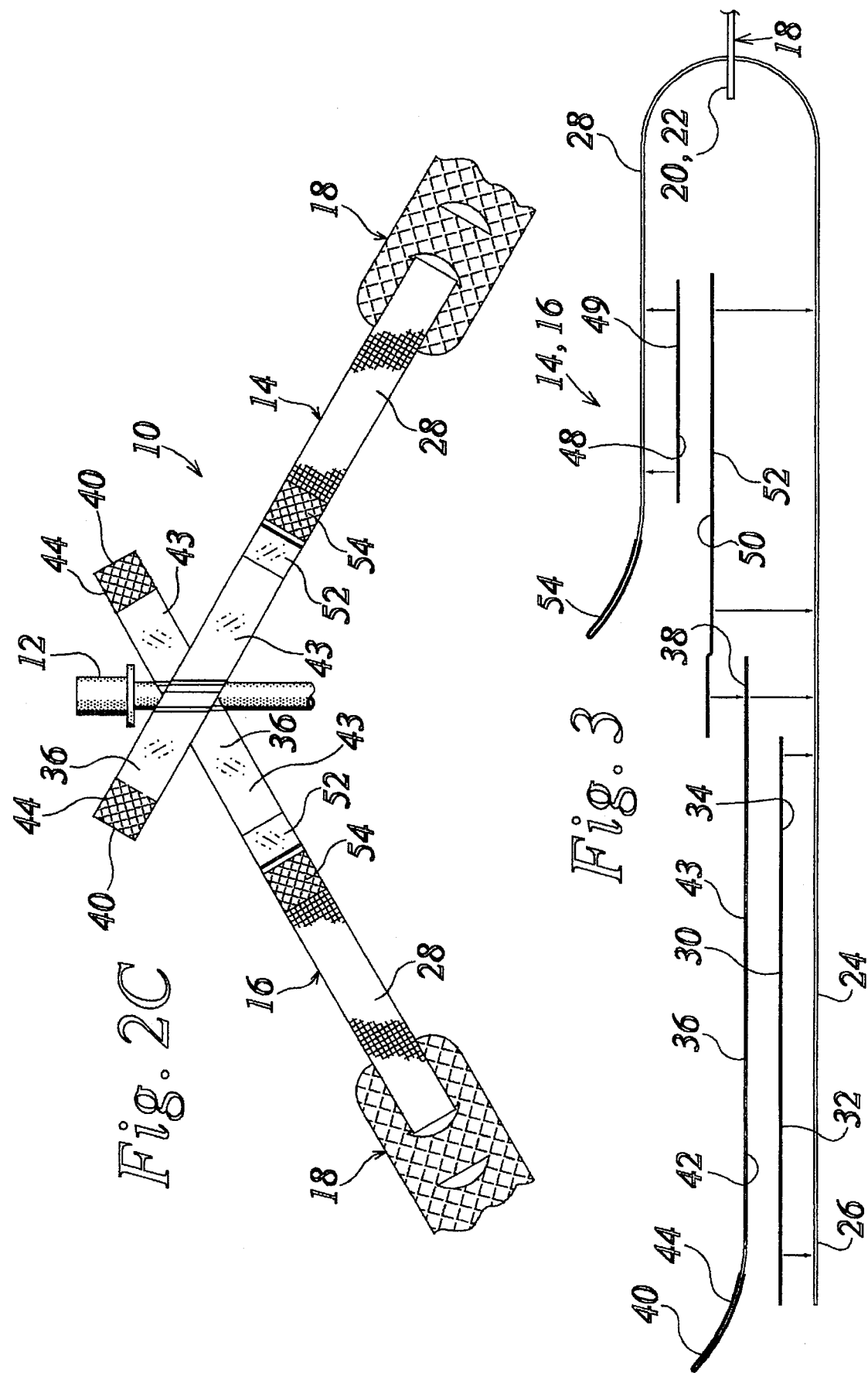

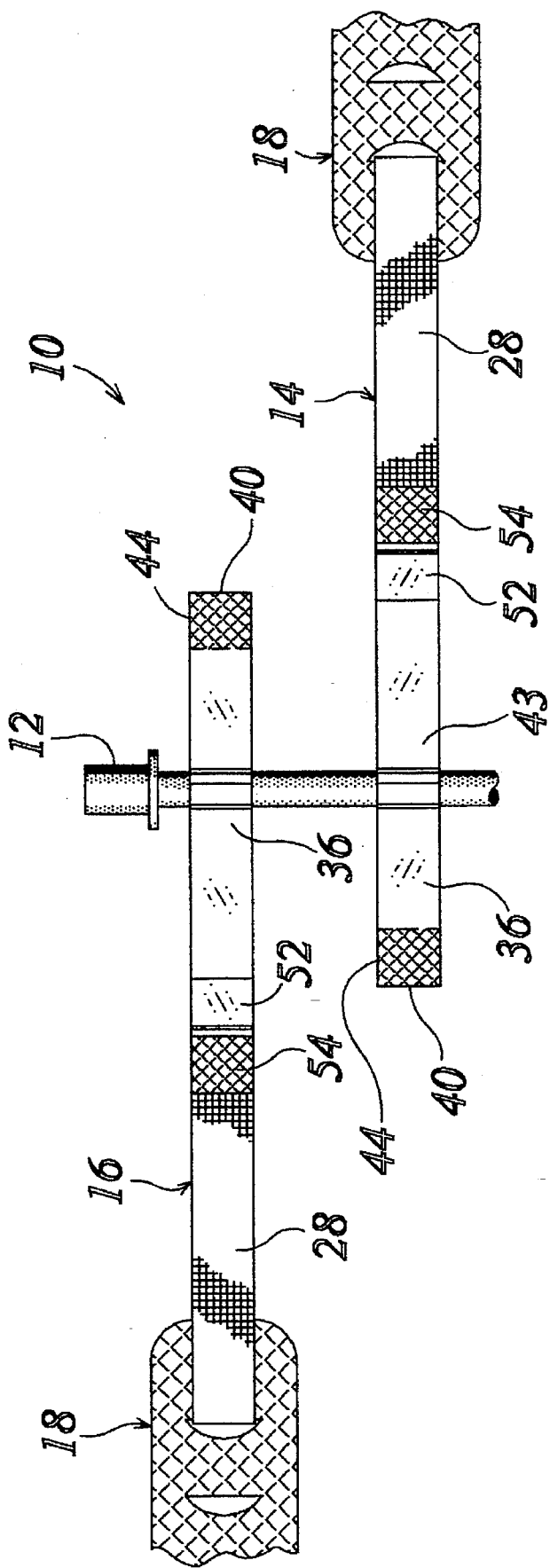

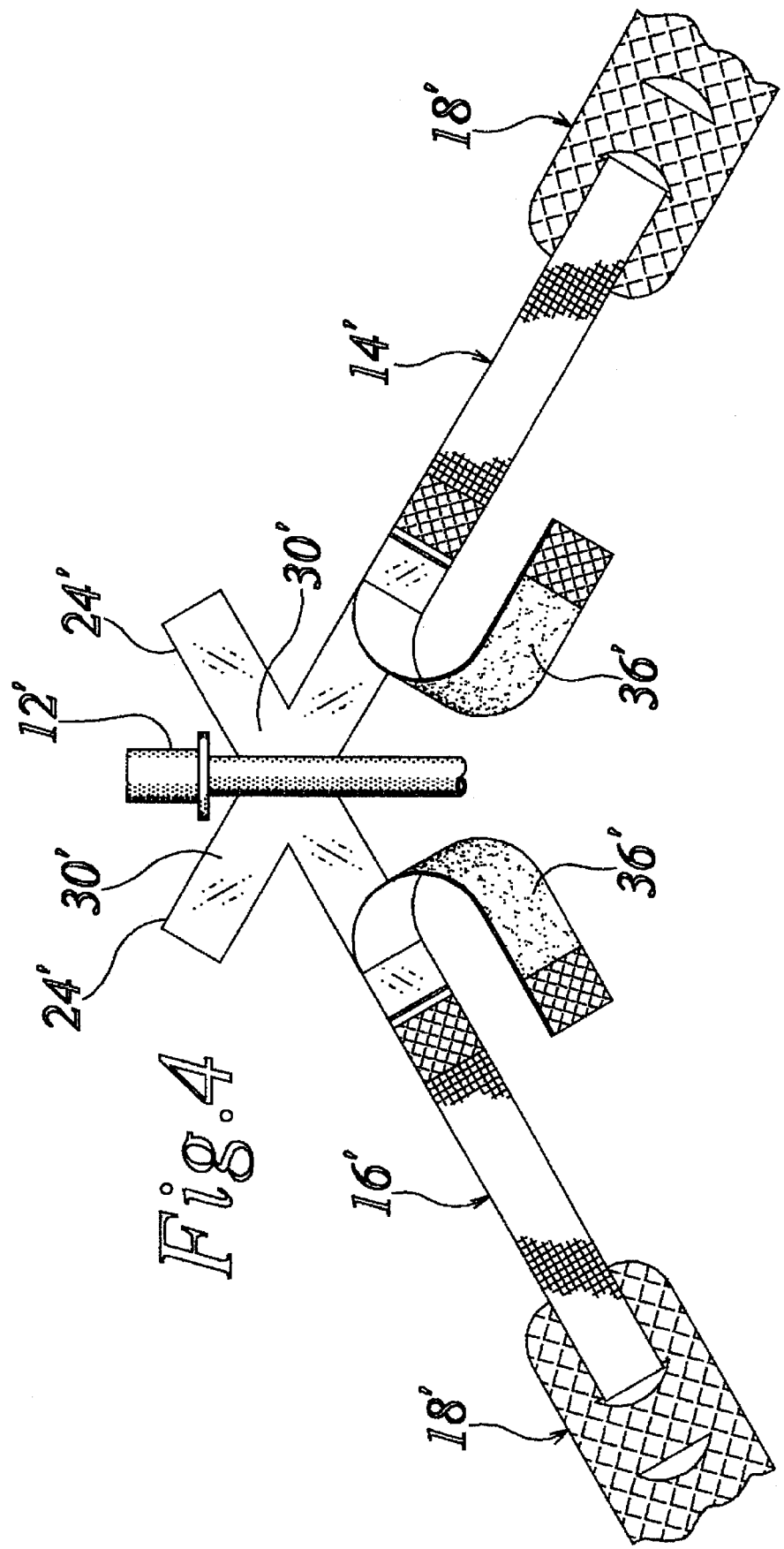

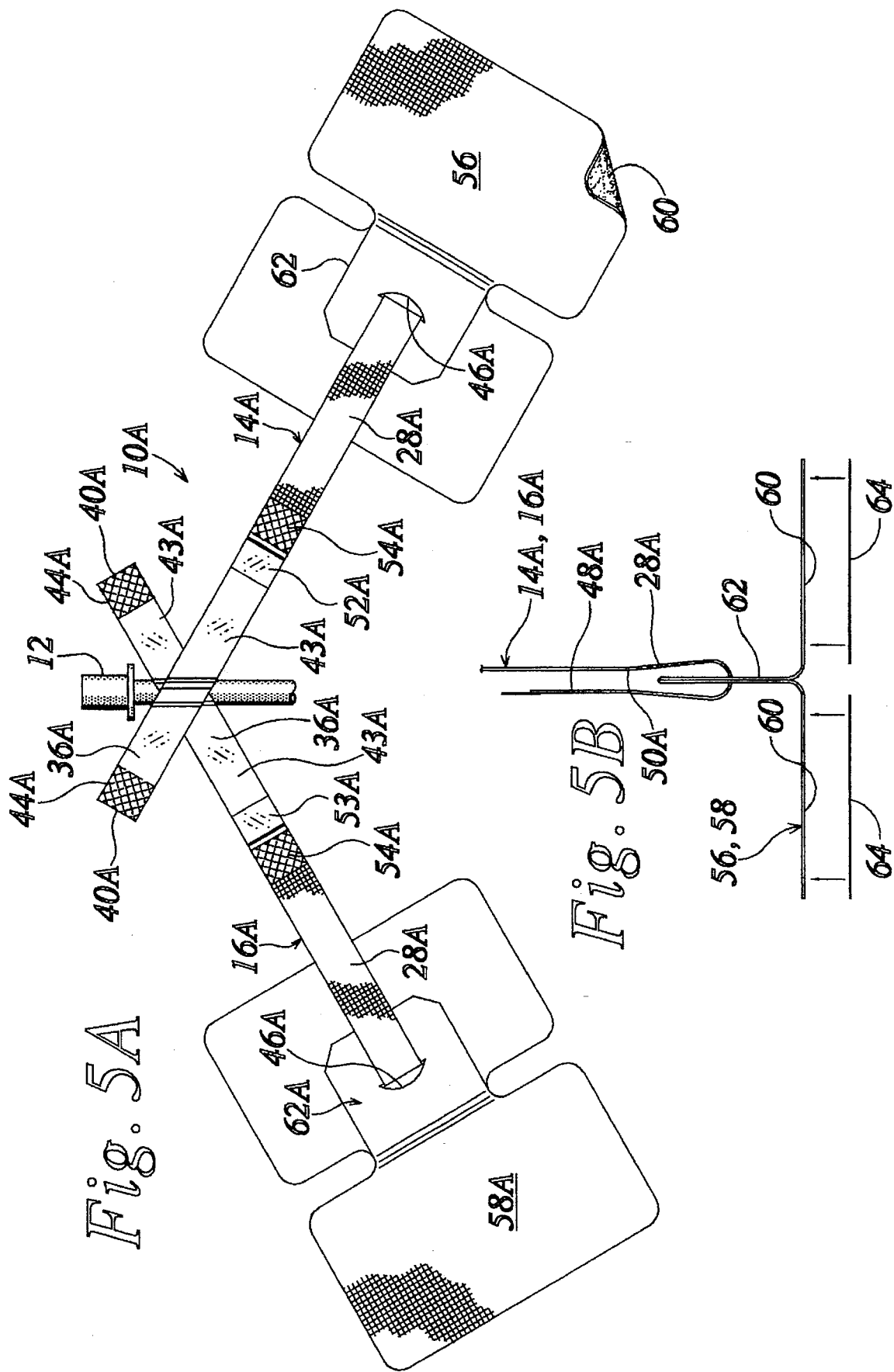

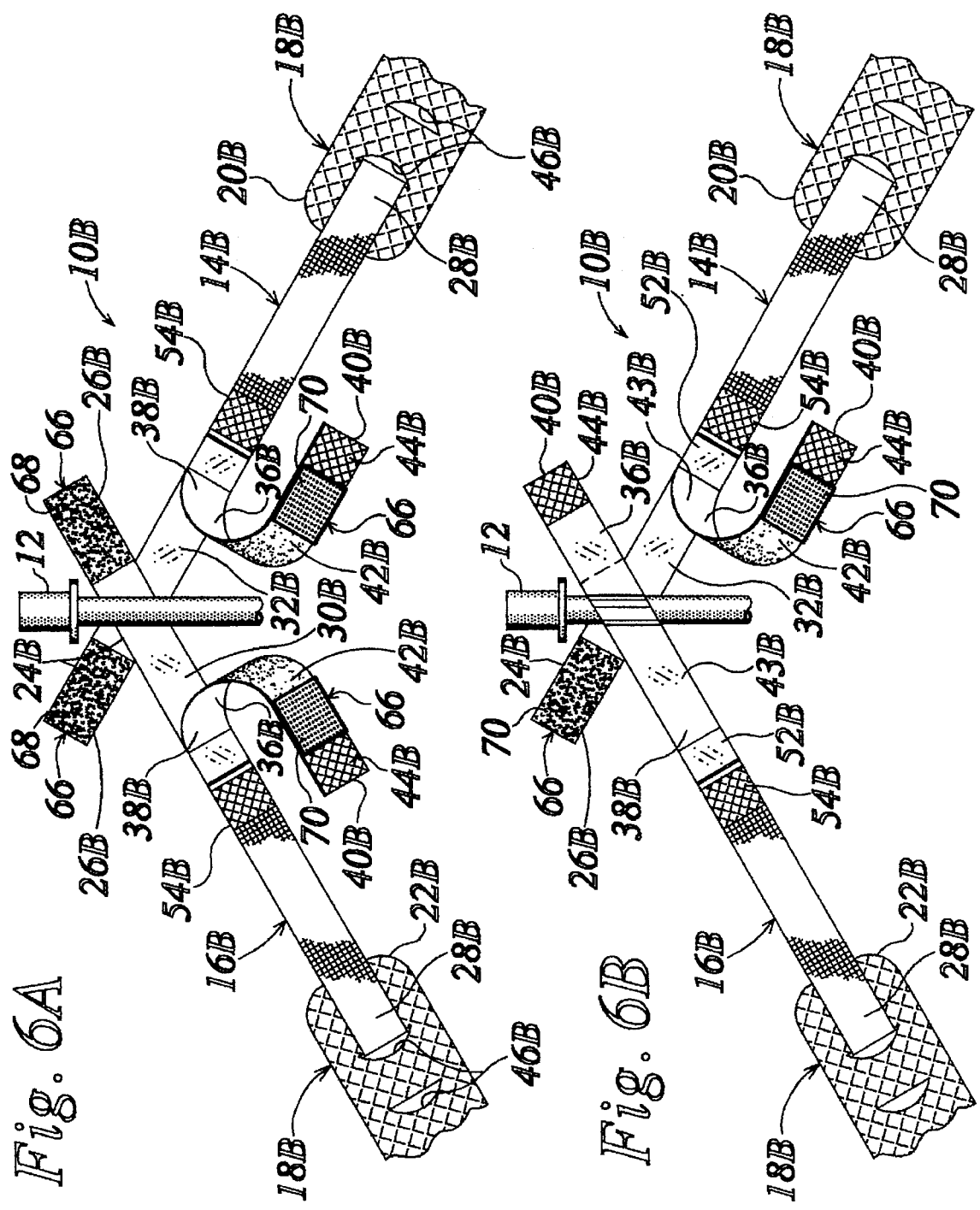

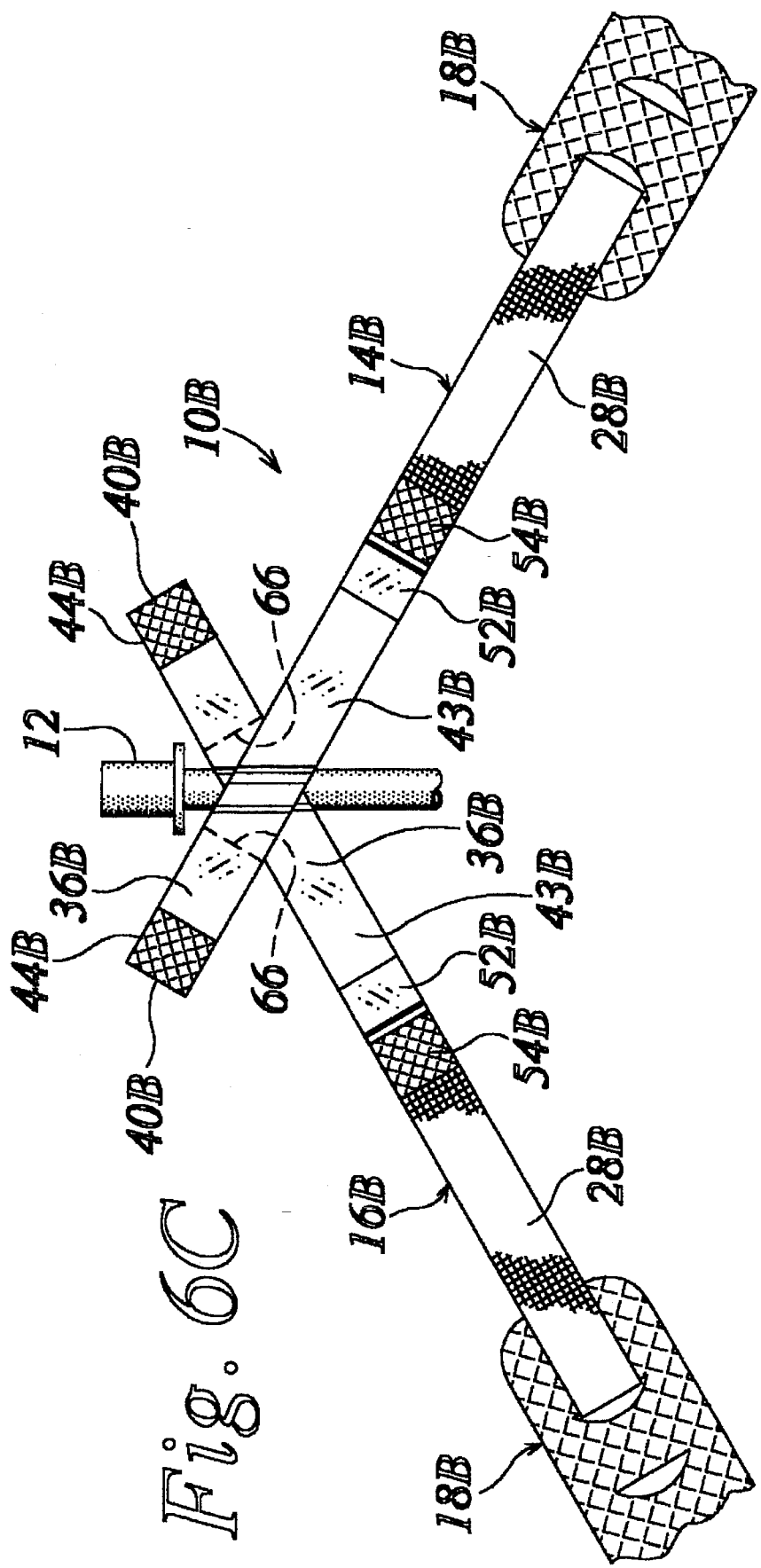

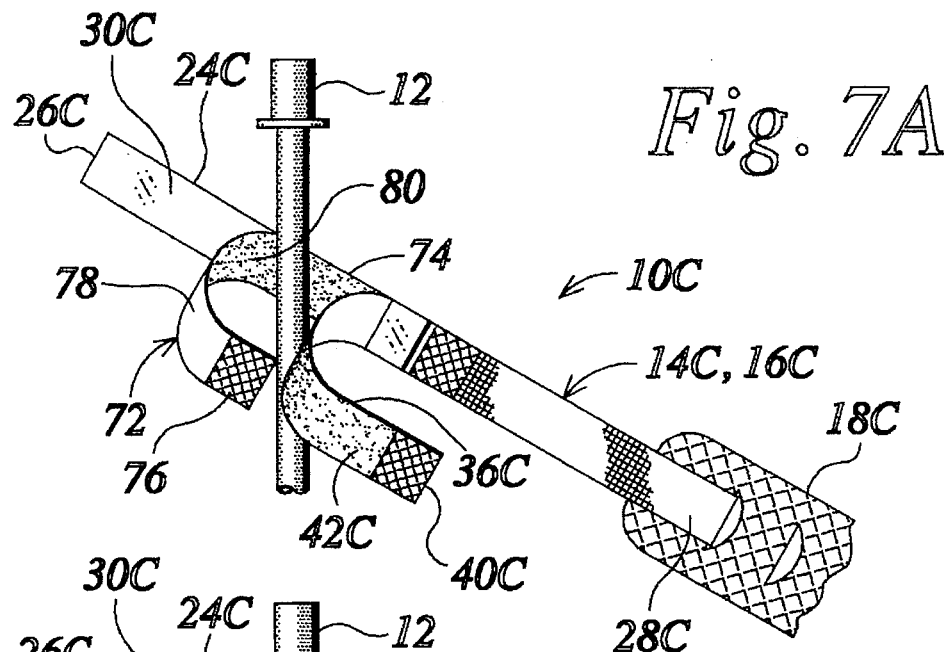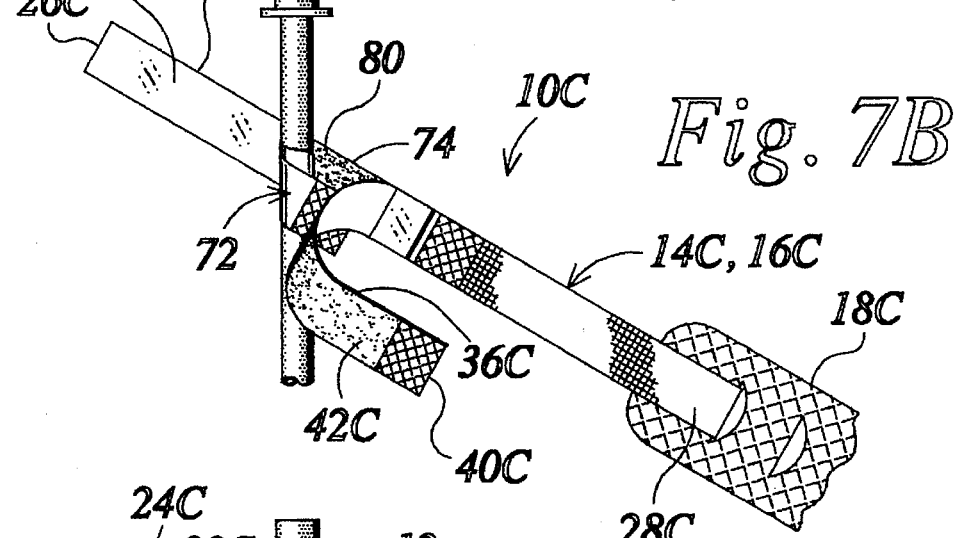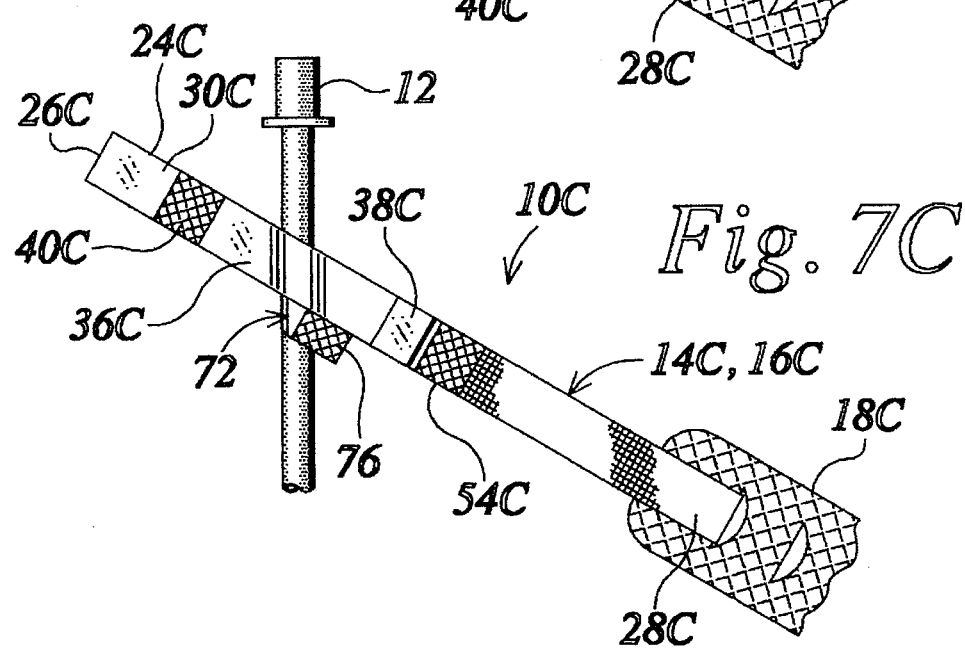

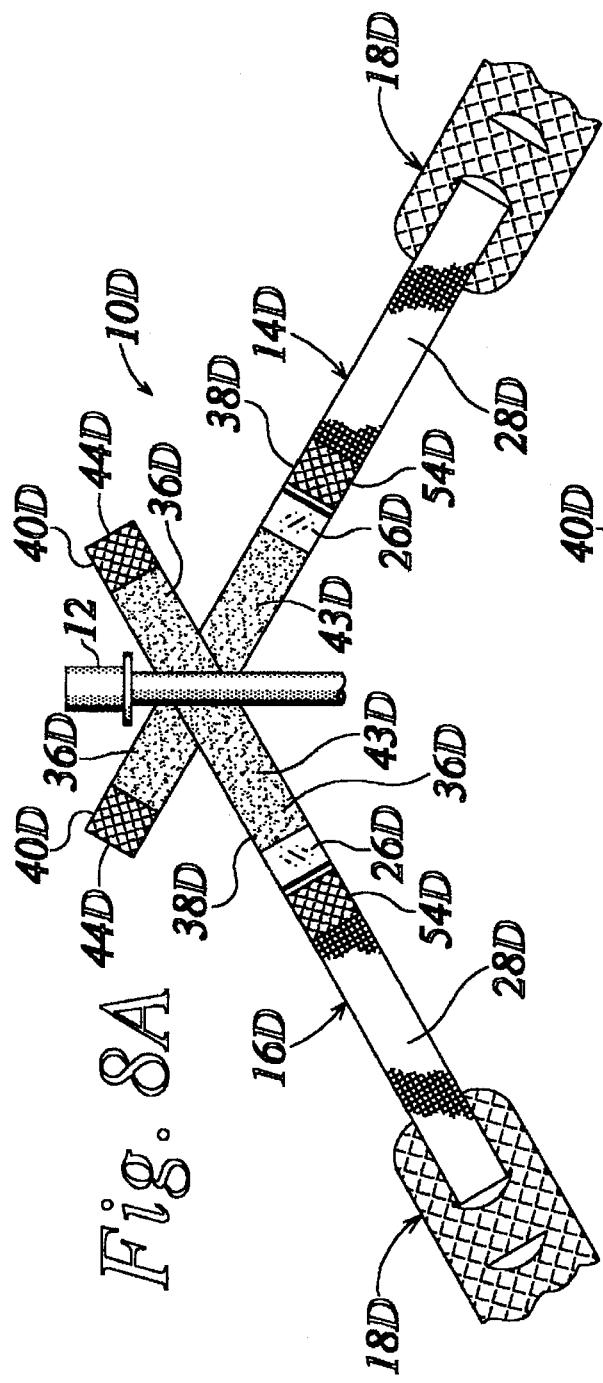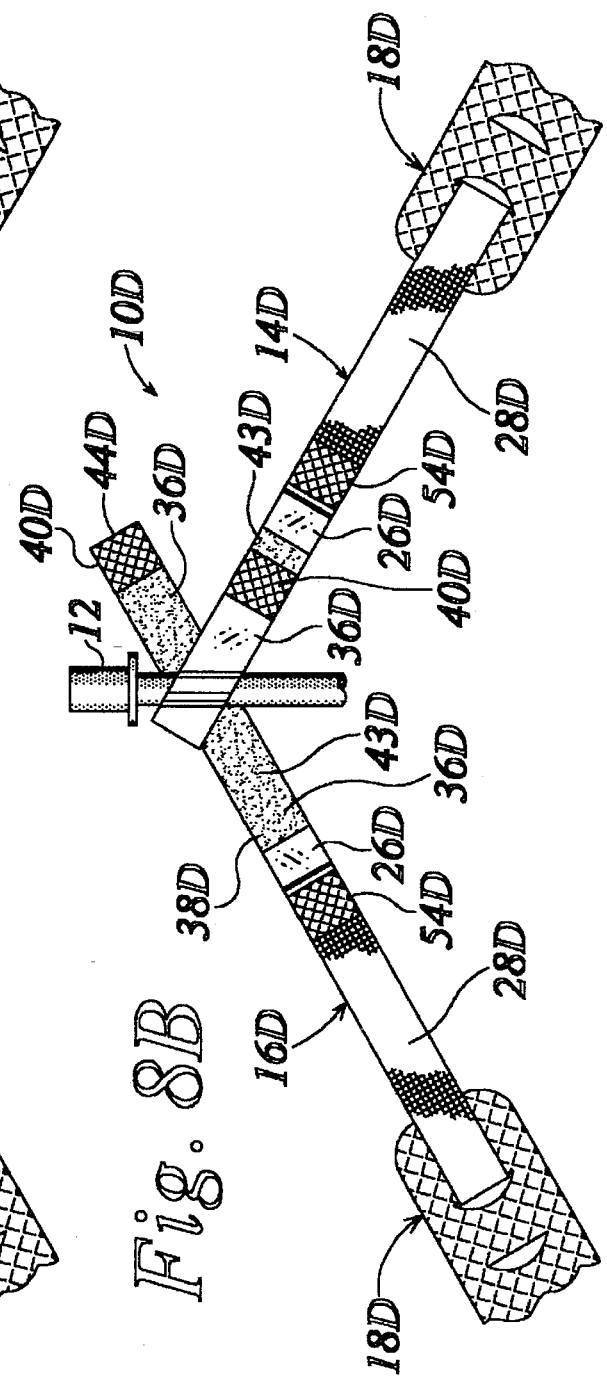

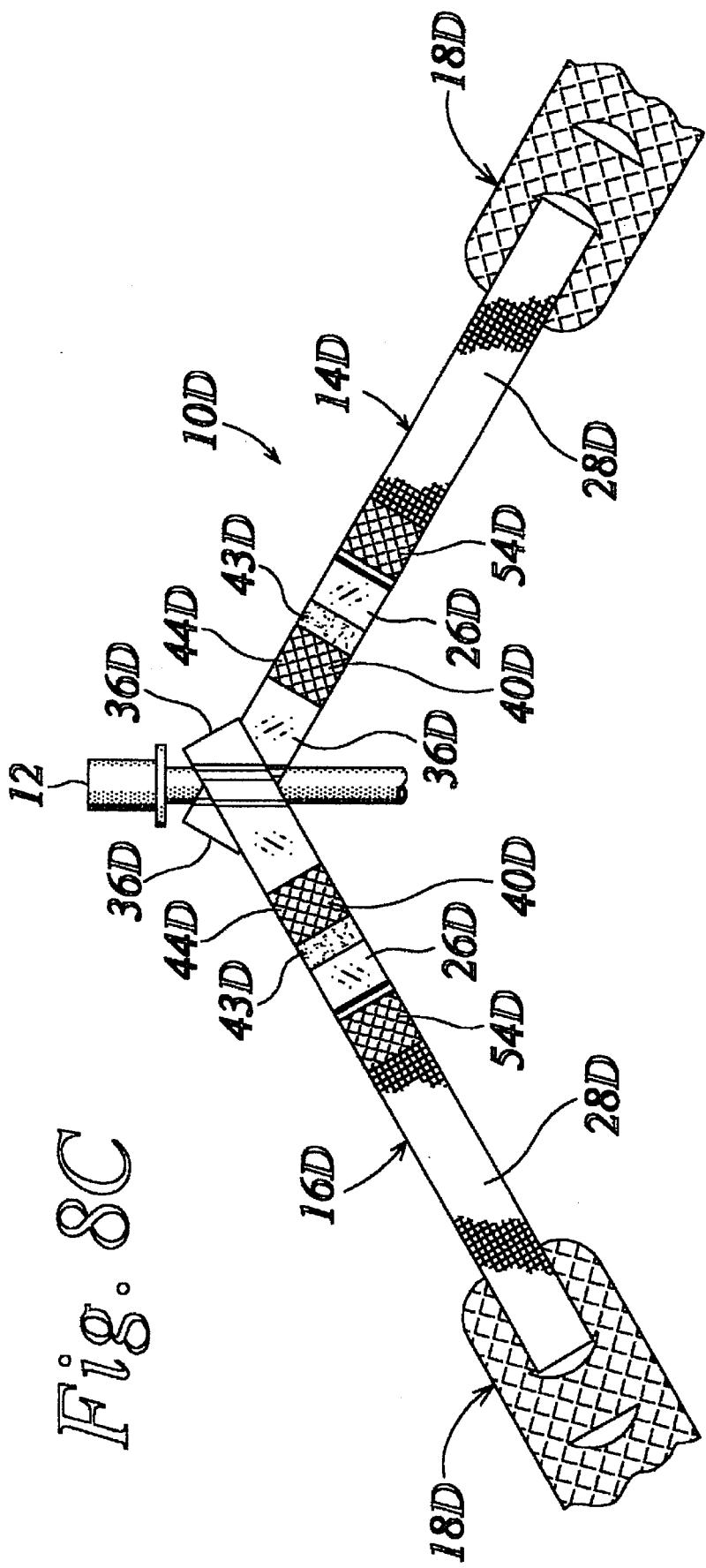

ENDOTRACHEAL TUBE HOLDING DEVICE AND ASSOCIATED TUBE HOLDING METHOD

This application is a continuation-in-part of my U.S. patent application Ser. No. 08/328,685 filed Oct. 25, 1994 now U.S. Pat. No. 5,448,985.

TECHNICAL FIELD

This invention relates to an endotracheal tube holding device for securing the position of a endotracheal tube as such tube is received through a nostril or the mouth of a patient. In this particular invention the tube holding device includes first and second tube engaging apparatus which engage the endotracheal tube proximate the point at which such tube enters the body of the patient.

BACKGROUND ART

The use of endotracheal tubes to effect artificial ventilation of a patient's lungs is a common medical procedure. Such tubes can be inserted thought a nostril or mouth of a patient. However, once the endotracheal tube is inserted, difficulties can arise in stabilizing the position of the tube such that it is not inadvertently removed, and such that movement of the tube does not cause discomfort to the patient. Accordingly, attempts have been made to devise endotracheal tube holding devices which secure the position of the tube once it has been inserted. Certain examples of such devices are disclosed in U.S. Pat. Nos. 5,009,227; 4,774,944; 4,744,358; 4,489,723; 4,351,311; 4,249,529; and 3,927,676. Further, the Dale Endotracheal Tube Holder, manufactured by Dale Medical Products, Inc., of Plainville, Mass., is an example of such a device. However, the various holding devises have proven to be either ineffective for holding the tube in place, difficult to use, and/or expensive. Further, such devices are rarely suitable for use with both oral exiting tubes and nasal exiting tubes. Therefore, commonly the medical caretaker will improvise and use an adhesive tape method whereby a length of adhesive tape is wrapped around the patient's head, then split into two segments, and the segments are wrapped around the tube, with the remaining tape ends secured across the lip or over the nose of the patient. But, the adhesive tape rarely stays bonded to the skin or the tube for the desired length of time, particularly where silicone tubing is being utilized. In this regard, silicone is becoming the preferred fabricating material for endotracheal tubes, but adhesive tape does not bond well with the surface of a silicone tube. Other tube holding devices are disclosed in U.S. Pat. Nos. 4,932,9434; 836,200; 5,037,397; 4,823,789; 3,046,989; U.S. Pat. No. Des. 310,721; 5,215,532; 4,690,675; 4,583,976; 4,333,468; 4,142,527; 4,120,304; 3,977,407; 3,826,254; 3,713,448 4,327,716; 4,569,348; 4,671,787; 4,799,923; 4,822,342; 5,038,778; 5,042,477; 5,135,506; 5,163,914; and 5,306,233.

Therefore, it is an object of the present invention to provide an endotracheal tube holding device for securing the position of an endotracheal tube.

It is another object of the present invention to provide an endotracheal tube holding device for securing the position of an endotracheal tube which utilizes friction and pressure to hold the endotracheal tube as well as adhesive surface bonding.

Yet another object of the present invention is to provide an endotracheal tube holding device for securing the position of an endotracheal tube which can be used with both orally exiting endotracheal tubes and nasal exiting endotracheal tubes.

Still another object of the present invention is to provide an endotracheal tube holding device for securing the position of an endotracheal tube which can be quickly and easily installed and which allows subsequent adjustment of the position of the tube after initial installation.

Still another object of the present invention is to provide an endotracheal tube holding device for securing the position of a endotracheal tube which is inexpensive to manufacture such that it is economically disposable.

SUMMARY OF THE INVENTION

Other objects and advantages will be accomplished by the present invention which provides an endotracheal tube holding device for securing the position of an endotracheal tube. The tube holding device includes first and second tube engaging apparatus, each of which includes a foundation strap having an outer bonding surface proximate its distal end portion. Each of the tube engaging apparatus also includes a tube engaging strap for releasably engaging and securing the position of the endotracheal tube. The tube engaging straps define a proximal end secured to the operatively associated foundation strap and an inner surface coated with an adhesive for releasably engaging the outer bonding surface of the foundation strap with the endotracheal tube therebetween. Also provided is a securing strap having a first end portion for releasably engaging the proximal end portion of the foundation strap of the first tube engaging apparatus and a second end portion for releasably engaging the proximal end portion of the foundation strap of the second tube engaging apparatus.

In accordance with the method of tire present invention the foundation strap of the first robe engaging apparatus is placed the point at which the endotracheal tube enters the body of the patient. The foundation strap of the second tube engaging apparatus is then placed diagonally across the foundation strap of the first tube engaging apparatus, and the tube engaging straps are secured to the bonding surfaces of their operatively associated foundation straps with one engaging strap received over the other and with the endotracheal tube disposed between the tube engaging straps and the foundation straps. Further, the securing strap is placed around the body of the patient, with its first end portion releasably engaging the proximal end portion of one foundation strap and its second end portion releasably engaging the proximal end portion of the other foundation strap, thereby facilitating the securing of the tube holding device on the body of the patient.

BRIEF DESCRIPTION OF THE DRAWINGS

The above mentioned features of the invention will be more clearly understood from the following detailed description of the invention read together with the drawings in which:

FIG. 2A illustrates a partial front elevation view of an endotracheal tube holding device of the present invention.

FIG. 2B illustrates a partial front elevation view of an endotracheal tube holding device of the present invention.

FIG. 2C illustrates a partial front elevation view of an endotracheal tube holding device of the present invention.

FIG. 2D illustrates a partial front elevation view of an endotracheal tube holding device of the present invention.

FIG. 3 illustrates an exploded plan view of a tube engaging apparatus of an endotracheal tube holding device of the present invention.

FIG. 4 illustrates a partial front elevation view of a first alternate embodiment of an endotracheal tube holding device of the present invention.

FIG. 5A illustrates a front elevation view of a second alternate embodiment of an endotracheal tube holding device of the present invention.

FIG. 5B illustrates a partial plan view of the second alternate embodiment of an endotracheal tube holding device of the present invention.

FIG. 6A illustrates a partial front elevation view of a third alternate embodiment of an endotracheal tube holding device of the present invention.

FIG. 6B illustrates a partial front elevation view of the third alternate embodiment of an endotracheal tube holding device of the present invention.

FIG. 6C illustrates a partial front elevation view of the third alternate embodiment of an endotracheal tube holding device of the present invention.

FIG. 7A illustrates a partial perspective view of a fourth alternate embodiment of an endotracheal tube holding device of the present invention.

FIG. 7B illustrates a partial perspective view of the fourth alternate embodiment of an endotracheal tube holding device of the present invention.

FIG. 7C illustrates a partial perspective view of the fourth alternate embodiment of an endotracheal tube holding device of the present invention.

FIG. 8A illustrates a partial front elevation view of a fifth alternate embodiment of an endotracheal tube holding device of the present invention.

FIG. 8B illustrates a partial front elevation view of the alternate embodiment of an endotracheal tube holding device of the present invention.

FIG. 8C illustrates a partial front elevation view of the fifth alternate embodiment of an endotracheal tube holding device of the present invention.

BEST MODE FOR CARRYING OUT THE INVENTION

Figure 1:
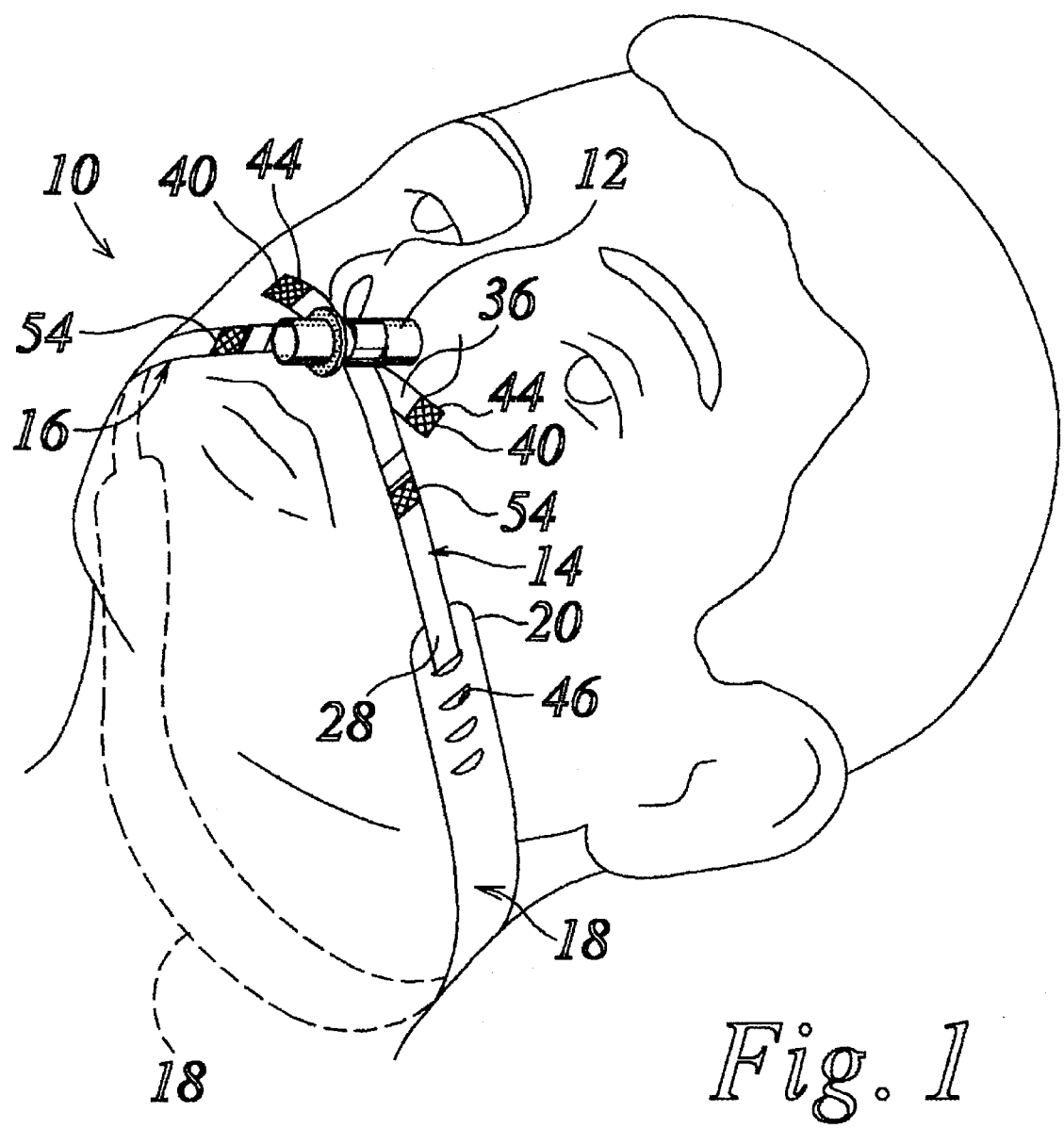
FIG. 1 illustrates perspective view of an endotracheal tube holding device of the present invention.

An endotracheal tube holding device incorporating various feature of the present invention is illustrated at 10 in the Figures. The device 10 is designed for securing the position of an endotracheal tube, such as the illustrated tube 12, as such tube is received through a nostril or the mouth of a patient. Whereas the device 10 is illustrated in FIG. 1 as being used to secure the position of an endotracheal tube 12 which is received through the nostril of a patient, it will be understood by those skilled in the art that the device 10 will serve to secure the position of endotracheal tubes which are inserted through the mouth of a patient as well.

The tube holding device I 0 includes first and second tube engaging apparatus 14 and 16, respectively, for releasably engaging a tube 12, as the tube 12 is positioned in the nostril or mouth of a patient. As will be discussed further below, the tube engaging apparatus 14 and 16 are secured on the opposite end portions 20 and 12 of a securing strap 18 which is receive around the patient's body proximate the head so as to hold the tube engaging apparatus 14 and 16 in place.

Each of the tube engaging apparatus 14 and 16 includes a flexible foundation strap 24 having a distal end portion 26 and a proximal end portion 28. Whereas in the preferred embodiment the foundation straps 24 are separately formed, it is anticipated that the foundation straps 24 can be integrally formed as illustrated at 24' in FIG. 4. Further, the straps 24 are preferably fabricated of a soft pliable material, such as a spun-bond polypropylene material which is soft, breathable, inexpensive, and comfortable to the patient. However, other suitable materials can be used if desired.

Each of the tube engaging apparatus 14 and 16 is provided with a smooth, substantially non-porous, outer bonding surface 30 proximate its distal end portion 26. As is best illustrated in FIG. 3, in the preferred embodiment a length of cellophane or plastic-backed adhesive tape 32 having an inner adhesive covered surface 34 (such as 3-$M^R$9921 bonding panel tape) is secured proximate the distal end portion 26 of the foundation strap 24 so as to provide the bonding surface 30.

Further, each of the tube engaging apparatus 14 and 16 also include a flexible tube engaging strap 36 for releasably engaging, and securing the position of a tube 12. The tube engaging straps 36 define a proximal end 38 and a distal end 40. The proximal end 38 of the strap 36 is secured to the operatively associated foundation strap 24, with the strap 36 being positioned such that the interior surface 42 of the strap 36 is engagable with the bonding surface 30. In this regard, at least a substantial portion of the inner surface 42 of the tube engaging strap 36 is coated with an adhesive such that the strap 36 can be selectively secured to the bonding surface 30 of the foundation strap 24 with a tube 12 disposed therebetween, or a tube 12 and a foundation strap 24 disposed therebetween. One suitable fabricating material for the straps 36 is 3-$M^R$9920 securing tape, but other suitable materials can be used if desired.

Thus, in securing an endotracheal tube 12 in accordance with the method of the present invention, the foundation strap 24 of the first tube engaging apparatus 14 is positioned between the tube 12 and the patient, with the foundation strap 24 of the second tube engaging apparatus 16 being positioned diagonally across the foundation strap 24 of the first engaging apparatus 14. (See FIG. 2A) The tube engaging straps 36 of the first and second tube engaging apparatus 14 and 16 are then releasably secured over the tube 12 so as to engage the tube 12 and the operatively associated bonding surface 30. (See FIG. 2B and 2C). Alternatively, a tube 12 can be secured by positioning the foundation strap 24 of the first tube engaging apparatus 14 between the tube 12 and the patient and positioning the operatively associated tube engaging strap 36 over the tube 12 and securing it to the foundation strap 24. The foundation strap 24 of the second tube engaging apparatus 16 is then positioned diagonally beneath the foundation strap 24 of the first tube engaging apparatus 14, and the tube engaging strap 36 of the second tube engaging apparatus 16 is positioned over the tube 12 and the other strap 36 and secured to the foundation strap 24 of the second tube engaging apparatus 16. It will be recognized that in certain circumstances both tube engaging straps 36 may not directly engage the tube 12 since one of the tube engaging straps 36 is received over the other and indirectly engages the tube 12 through its contact with the other tube engaging strap 36. Therefore, references herein to the tube engaging straps 36 engaging the tube 12 are intended to include both direct and indirect engagement of the tube 12.

Accordingly, the tube 12 is firmly secured between the diagonally crossing foundation straps 24 and diagonally crossing tube engaging straps 36. (See FIG. 2C). However, the tube 12 can be quickly and easily released by pulling back the tube engaging straps 36. In this regard, each of the engaging straps 36 is provided with a smooth, substantially non-porous outer bonding surface 43 which is releasably receptive of the adhesive covered interior surface 42 of the other engaging strap 36. Thus, when the tube 12 is being released, the overlapping strap 36 will disengage from the underlying strap 36 without damage to the device 10. In the preferred embodiment the bonding surface 43 is defined by a length of cellophane or plastic-backed tape such as 3-M$^R$9921 bonding panel tape. Further, it will be noted that in the preferred embodiment the distal ends 40 of the tube engaging straps 36 carry tab members 44 each of which defines an area which is free of adhesive, and preferably of increased thickness, so as to facilitate the manipulation of the of the tube engaging straps 36.

Whereas in the preferred application of the method of the present invention the foundation straps 24 are disposed so as to diagonally cross one another, with the tube engaging straps 36 diagonally crossing as well, there may be circumstances which call for the first and second tube engaging apparatus 14 and 16 to engage a tube 12 at selectively spaced positions along the tube 12. An example of such a spaced engagement of the first and second tube engaging apparatus 14 and 16 with a tube 12 is illustrated in FIG. 2D.

As noted above, the securing strap 18 serves to secure the device 10 about the body of the patient proximate the head so as to maintain the position of the tube engaging apparatus 14 and 16, and, thus, the tube 12 engaged thereby. In this regard, in the preferred embodiment adjustable securing mechanisms are provided for securing the each of the tube engaging apparatus 14 and 16 to the opposite ends 20 and 22 of the securing strap 18 such that the length of the device 10 is adjustable to accommodate different patients.

More specifically, in the preferred embodiment of FIG. 3 the securing strap 18 is provided with selectively spaced openings 46 for selectively receiving therethrough the proximal end portions 28 of the tube engaging apparatus 14 and 16. Each of the proximal end portions 28 has an adhesive surface 48, which in the preferred embodiment is defined by a length of double sided adhesive tape 49, such as, for example, Flexcon H-566, 3 mil tape. Further, the foundation straps 24 are each provided with a smooth, substantially non-porous, outer bonding surface 50 to which the adhesive surface 48 can be releasably secured after the proximal end portion 28 has been received through an opening 46. In the preferred embodiment the bonding surfaces 50 are defined by lengths of plastic or cellophane tape 52, such as, for example, 3-M$^R$9921 bonding panel tape, which are secured to the foundation straps 24.

Thus, it will be recognized that by selecting the openings 46 to be used, and by selecting the position along the bonding surfaces 50 at which the adhesive surfaces 48 are secured, the effective length of the device 10 can be changed to accommodate different patients and to effect a tightening or loosening of the device 10 as it is positioned about a patient's body. It will be noted that the proximal end portions 28 of the foundation straps 24 can be provided with tab members 54 which define an area which is free of adhesive, and preferably of increased thickness, so as to facilitate the manipulation of the proximal end portions 28 and the adjustable securing of the tube engaging apparatus 14 and 16 to the securing strap 18. It will also be noted that in the preferred embodiment the length of tape 52 is of sufficient length to extend over the proximal end portion 38 of the operatively associated tube engaging strap 36 such that it serves to secure the strap 36 to the foundation strap 24.

In the preferred embodiment the securing strap 18 is fabricated of a spun-bond polypropylene material which is soft, breathable, inexpensive, and comfortable to the patient. However, other suitable materials can be used if desired. Moreover, the above notwithstanding, it is contemplated that the securing strap 18 can be integrally formed with the foundation straps 24, such that foundation strap portions are defined at the opposite ends of an elongated securing strap 18 Accordingly, the above described tube holding device having separately formed foundations straps 24 and securing strap 18 is merely illustrative of one preferred embodiment.

In FIGS. 5A and 5B an alternate embodiment of the tube holding device of the present invention is illustrated at 10A. For convenience, components and features of the tube holding device 10A which are common to the above-described tube holding device 10 will be referenced in the Figures with common numerals followed by the alphabetic character "A".

In the embodiment of FIGS. 5A and 5B the device 10A is secured to the body of a patient with first and second adhesive members 56 and 58, respectively, instead of with a securing strap 18. In this regard, each of the adhesive members 56 and 58 defines an inner surface 61), at least a substantial portion of which is coated with an adhesive for releasably bonding the adhesive members 56 and 58 to the patient. Of course, such adhesive bonding can be accomplished by a direct bond with the skin of the patient or by bonding the members 56 and 58 to the clothing of the patient. Each of the adhesive members 56 and 58 also define a tab portion 62 provided with an opening 46A for receiving therethrough the proximal end portions 28A of the operatively associated tube engaging apparatus 14A or 16A. Accordingly, the proximal end portions 28A can be secured to the adhesive members 56 and 58 by inserting the proximal end portions 28A through the openings 46A and securing the adhesive surfaces 48A to the bonding surfaces 50A provided on the foundation straps 24A.

As illustrated in FIG. 5A-B, in the preferred embodiment the adhesive members 56 and 58 define a pair of joined adhesive panels in what is commonly referred to as a butterfly configuration. This configuration provides a large surface area for bonding, while allowing the members 56 and 58 to be readily folded for efficient packaging. However, it will be recognized that other configuration can be used. Further, the inner surfaces 60 are preferably provided with cover panels 64 for protecting the adhesive on the surfaces 60 prior to use, with the panels 64 being removed prior to use to expose the adhesive.

In FIGS. 6A-C another alternate embodiment of the present invention is illustrated at 10B. For convenience, components and features of the tube holding device 10B which are common to the above-described tube holding device 10 will be referenced in the Figures with common numerals followed by the alphabetic character "B".

As illustrated, the device 10B is provided with hook and loop fasteners 66 which releasably secure the distal ends 40B of the tube engaging straps 36B to the distal end portions 26B of the foundation straps 24B. More specifically, a first component 68 (which in the preferred embodiment is the loop component) of each fastener 66 is disposed on the distal end portion 26B of the operatively associated foundation strap 24B, and a second component 70 (which in the preferred embodiment is the hook component) of each fastener 66 is disposed on the distal end 40B of the operatively associated tube engaging strap 36B. Thus, whereas the adhesive on the inner surfaces 42B of the engaging straps 36B serves to releasably hold the tube 12 in the desired position, the releasable securing of the engaging straps 36B to the operatively associated foundation straps 24B is accomplish by securing the second component 70 to the first component 68. With respect to this alternate fastening means, it will be recognized that the hook and loop fastener 66 can be used in conjunction with various other embodiments of the device of the present invention described herein to secure the engaging straps to the operatively associated foundation straps while the tube 12 is held in place by an adhesive bond.

Yet another alternate embodiment of the device of the present invention is illustrated at 10C in FIGS. 7A–7C. For convenience, components and features of the tube holding device 10C which are common to the above-described tube holding device 10 will be referenced in the Figures with common numerals followed by the alphabetic character "C".

In addition to the tube engaging straps 36C, the tube engaging members 14C and 16C of the tube holding device 10C are provided with further tube engaging straps 72 which are disposed between the engaging straps 36C and the foundation straps 24C. The further tube engaging straps 72 each define a proximal end 74 and a distal end 76. The proximal end 74 of the each further strap 72 is secured to the operatively associated foundation strap 24C, with the further strap 72 being oriented such that the inner surface 78 of the strap 72 overlays the bonding surface 30C when the strap 72 is not in use. Each of the further straps 72 also defines an outer surface 80, at least a substantial portion of which is coated with an adhesive. Thus, as illustrated in FIG. 7A, the tube 12 can be positioned between the straps 36C and 72, and the strap 72 can be secured about the tube 12 as illustrated in FIG. 7B. As illustrated in FIG. 7C, the strap 36C is then secured over the further tube engaging strap 72 proximate the point at which it engages the tube 12, and is adhesively bonded to the bonding surface 30C of the foundation strap 24C. Accordingly, the tube engaging strap 36C serves to releasably secure the position of the further tube engaging strap 72 and the tube 12 secured therein.

Further, it will be recognized that once the tube 12 is secured in one tube engaging apparatus 14C or 16C, the other tube engaging apparatus 14C or 16C can be secured by securing its further tube engaging strap 72 about the tube 12, and about the further tube engaging strap 72 of the initially installed apparatus. The tube engaging strap 36C of the subsequently installed apparatus can then be secured over both further tube engaging straps 72 and the tube 12 and adhesively bonded to the operatively associated bonding surface 30C. Alternatively, the tube engaging apparatus 14C and 16C can be installed at spaced locations along the tube 12 if desired.

A further alternate embodiment of the device of the present invention is illustrated at 10D in FIGS. 8A–8C. For convenience, components and features of the tube holding device 10D which are common to the above-described tube holding device 10 will be referenced in the Figures with common numerals followed by the alphabetic character "D".

In the illustrated embodiment of FIGS. 8A–C, the proximal ends 38D of the tube engaging straps 36D are secured to the distal end portions 26D of the operatively associated foundation straps 24D. Further, rather than the inner surfaces 42D of the straps 36D being provided with adhesive, as in the case of the device 10, at least a substantial portion of the outer surfaces 43D of the straps 36D are provided with an adhesive, as best illustrated in FIG. 8A. Accordingly, pursuant to one application of the tube holding device 10D, the tube 12 is position adjacent the outer surfaces 43D of the straps 36D as illustrated in FIG. 8A. As illustrated in FIG. 8B, the distal end 40D of a first strap 36D is then folded back over the tube 12 and the outer surface 43D proximate the distal end 40D of the first strap 36D is adhesively bonded to the outer surface 43D of such strap 36D proximate the proximal end 38D. The distal end 40D of a second strap 36D is then folded back over both the first strap 36D and the tube 12, and the outer surface 43D of the second strap 36D is adhesively bonded to the outer surface of the second strap 36D proximate the proximal end 38D. Accordingly, the straps 36D are adhesively bonded to the tube 12 and to each other.

However, it will be recognized with respect to the device 10D that the apparatus 14 and 16 can engage the tube 12 at selectively spaced positions along the tube 12, as discussed above with resect to the device 10 and FIG. 2D.

In light of the above it will be recognized that the present invention provides an endotracheal tube holding device and an associated method having great advantages over the prior art. In this regard, the endotracheal tube holding device of the present invention secures the position of a endotracheal tube not only through adhesive surface bonding, but through friction and pressure as the tube is positioned between the foundation straps and tube engaging straps. Accordingly, if the adhesive bond fails, the tube remains securely positioned in the device. The endotracheal tube holding device of the present invention can be used with both orally exiting endotracheal tubes and nasal exiting endotracheal tubes, and can be quickly and easily installed. Moreover, the device allows subsequent adjustments of the position of the tube after initial installation. It will also be noted that the holder is extremely thin, strong and durable, and the entire device can be quickly washed, dried and reinstalled, yet can be inexpensively manufactured so as to be economically disposable.

While a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. An endotracheal tube holding device for securing the position of an endotracheal tube, said tube holding device comprising:

a first tube engaging apparatus adapted for releasably engaging an endotracheal tube, said first tube engaging apparatus including a first foundation strap portion having a first distal end portion, said first tube engaging apparatus having a first tube engaging strap for releasably engaging and securing the position of the endotracheal tube, said first tube engaging strap defining a proximal end secured to said first foundation strap portion, and at least one of the first foundation strap portion and the first tube engaging strap including an adhesive-coated surface portion for releasably engaging the endotracheal tube; and a second tube engaging apparatus adapted for releasably securing the position of an endotracheal tube, said second tube engaging apparatus including a second foundation strap portion having a distal end portion, said second tube engaging apparatus having a second tube engaging strap for securing the position of the endotracheal tube, said second tube engaging strap defining a proximal end secured to said second foundation strap portion, and at least one of the second foundation strap portion and the second tube engaging strap including an adhesive-coated surface portion for releasably securing the position of the endotracheal tube.

2. An endotracheal tube holding device for securing the position of an endotracheal tube, said tube holding device comprising:
   a first tube engaging apparatus adapted for releasably engaging an endotracheal tube, said first tube engaging apparatus including a first foundation strap having a distal end portion and a proximal end portion, said first tube engaging apparatus having a first tube engaging strap for releasably engaging and securing the position of the endotracheal tube, said first tube engaging strap defining a proximal end secured to said first foundation strap, and at least one of the first foundation strap and the first tube engaging strap including an adhesive-coated surface portion for releasably engaging the endotracheal tube;
   a second tube engaging apparatus adapted for releasably engaging an endotracheal tube, said second tube engaging apparatus including a second foundation strap having a distal end portion and a proximal end portion, said second tube engaging apparatus having a second tube engaging strap for releasably engaging and securing the position of the endotracheal tube, said first tube engaging strap defining a proximal end secured to said second foundation strap, and at least one of the second foundation strap and the second tube engaging strap including an adhesive-coated surface portion for releasably engaging the endotracheal tube; and
   a securing mechanism for releasably securing said first and second tube engaging apparatus to a patient.

3. The endotracheal tube holding device of claim 2 wherein said securing mechanism includes a first adhesive member secured to said proximal end portion of said first foundation strap for releasably engaging the patient, and a second adhesive member secured to said proximal end portion of said second foundation strap for releasably engaging the patient.

4. The endotracheal tube holding device of claim 3 wherein said first adhesive member defines a tab portion for releasably engaging said proximal end portion of said first foundation strap, and wherein said second adhesive member defines a further tab portion for releasably engaging said proximal end portion of said second foundation strap.

5. The endotracheal tube holding device of claim 4 wherein said tab portion of said first adhesive member defines an opening for receiving said proximal end portion of said first foundation strap therethrough, and said further tab portion of said second adhesive member defines an further opening for receiving said proximal end portion of said second foundation strap therethrough, and wherein said first foundation strap is provided with a first adhesive surface portion for releasably engaging said first foundation strap along a first bonding surface selectively spaced from said first adhesive surface portion whereby said first foundation strap is releasably secured to said tab portion of said first adhesive member, and said second foundation strap is provided with a second adhesive surface portion for releasably engaging said second foundation strap along a second bonding surface provided on said second foundation strap selectively spaced from said second adhesive surface portion whereby said second foundation strap is releasably secured to said further tab portion of said second adhesive member.

6. The endotracheal tube holding device of claim 5 wherein said first and second adhesive members each define a pair of adhesive coated panels such that each said first and second adhesive member defines a butterfly configuration.

7. The endotracheal tube holding device of claim 2 wherein said first tube engaging strap defines a distal end portion, and said first tube engaging apparatus is provided with a first hook and loop fastener for releasably securing said distal end portion of said first tube engaging strap to said distal end portion of said first foundation strap, and wherein said second tube engaging strap defines a distal end portion, and said second tube engaging apparatus is provided with a second hook and loop fastener for releasably securing said distal end portion of said second tube engaging strap to said distal end portion of said second foundation strap.

8. The endotracheal tube holding device of claim 7 wherein said first hook and loop fastener includes a loop component disposed at said distal end portion of said first foundation strap and a hook component disposed at said distal end portion of said first tube engaging strap, and wherein said second hook and loop fastener includes a loop component disposed at said distal end portion of said second foundation strap and a hook component disposed at said distal end portion of said second tube engaging strap.

9. The endotracheal tube holder of claim 2 wherein said first tube engaging apparatus includes a further tube engaging strap disposed between said first foundation strap and said first tube engaging strap, said further tube engaging strap defining a proximal end secured to said first foundation strap and defining an outer adhesive-coated surface for engaging the endotracheal tube, and wherein said second tube engaging apparatus includes a further tube engaging strap disposed between said second foundation strap and said second tube engaging strap, said further tube engaging strap of said second tube engaging apparatus defining a proximal end secured to said second foundation strap and defining an outer adhesive-coated surface for securing the position of the endotracheal tube.

10. The endotracheal tube holder of claim 9 wherein said further tube engaging strap of said first tube engaging apparatus defines an inner adhesive-coated surface for engaging said first foundation strap, and said further tube engaging strap of said second tube engaging apparatus defines an inner adhesive-coated surface for engaging said second foundation strap.

11. The endotracheal tube holding device of claim 2 wherein said first tube engaging strap has an outer surface defining said adhesive-coated surface portion, and wherein said second tube engaging strap has an outer surface defining said adhesive-coated surface portion of said second tube engaging strap.

12. An endotracheal tube holding device for securing the position of an endotracheal tube, said tube holding device comprising:
   a first tube engaging apparatus adapted for releasably engaging an endotracheal robe, said first tube engaging apparatus including a first foundation strap having a distal end portion and an outer bonding surface proximate said distal end portion, said first tube engaging apparatus having a first tube engaging strap for releasably engaging and securing the position of the endotracheal tube, said first tube engaging strap defining a proximal end secured to said first foundation strap and an inner surface, at least a portion of which is coated with an adhesive for releasably engaging said outer bonding surface;
   a second tube engaging apparatus adapted for releasably engaging an endotracheal tube, said second tube engaging apparatus including a second foundation strap having a distal end portion and a further outer bonding surface proximate said distal end portion of said second foundation strap, said second tube engaging apparatus having a second tube engaging strap for releasably engaging and securing the position of the endotracheal tube, said second tube engaging strap defining a proximal end secured to said second foundation strap and an inner surface, at least a portion of which is coated with an adhesive for releasably engaging said further outer bonding surface with the endotracheal tube therebetween;

A securing mechanism for releasably securing said first and said tube engaging apparatus to a patient, said securing mechanism including a first adhesive member secured to said proximal end portion of said first foundation strap for releasably engaging the patient, and a second adhesive member secured to said proximal end portion of said second foundation strap for releasably engaging the patient, said first adhesive member defining a tab portion for releasably engaging said proximal end portion of said first foundation strap, and said second adhesive member defining a further tab portion for releasably engaging said proximal end portion of said second foundation strap.

13. The endotracheal tube holding device of claim 12 wherein said tab portion of said first adhesive member defines an opening for receiving said proximal end portion of said first foundation strap therethrough, and said further tab portion of said second adhesive member defines an further opening for receiving said proximal end portion of said second foundation strap therethrough, and wherein said first foundation strap is provided with a first adhesive surface portion for releasably engaging said first foundation strap along a first bonding surface selectively spaced from said first adhesive surface portion whereby said first foundation strap is releasably secured to said tab portion of said first adhesive member, and said second foundation strap is provided with a second adhesive surface portion for releasably engaging said second foundation strap along a second bonding surface provided on said second foundation strap selectively spaced from said second adhesive surface portion whereby said second foundation strap is releasably secured to said further tab portion of said second adhesive member.

14. An endotracheal tube holding device for securing the position of an endotracheal tube, said tube holding device comprising:

a first tube engaging apparatus adapted for releasably engaging an endotracheal tube, said first tube engaging apparatus including a first foundation strap having a distal end portion and a proximal end portion, said first tube engaging apparatus having a first tube engaging strap for releasably engaging and securing the position of the endotracheal tube, said first tube engaging strap defining a proximal end secured to said first foundation strap and an adhesive-coated surface portion for releasably engaging the endotracheal tube, said distal end portion of said first foundation strap carrying a first hook and loop fastener component, said first tube engaging strap defining a distal end portion carrying a second hook and loop fastener component for releasably engaging said first hook and loop fastener component thereby releasably securing said distal end portion of said first tube engaging strap to said distal end portion of said first foundation strap; and a second tube engaging apparatus adapted for releasably engaging an endotracheal tube, said second tube engaging apparatus including a second foundation strap having a distal end portion and a proximal end portion, said second tube engaging apparatus having a second tube engaging strap for releasably engaging and securing the position of the endotracheal tube, said first tube engaging strap defining a proximal end secured to said first foundation strap and an adhesive-coated surface portion for releasably engaging the endotracheal tube, said distal end portion of said second foundation strap carrying a further first hook and loop fastener component, said second tube engaging strap defining a distal end portion carrying a further second hook and loop fastener component for releasably engaging said further first hook and loop fastener component thereby releasably securing said distal end portion of said second tube engaging strap to said distal end portion of said second foundation strap.

15. An endotracheal tube holding device for securing the position of an endotracheal tube, said tube holding device comprising:

a first tube engaging apparatus adapted for releasably engaging an endotracheal tube, said first tube engaging apparatus including a first foundation strap having a distal end portion and an outer bonding surface proximate said distal end portion, said first tube engaging apparatus having a first tube engaging strap for releasably engaging and securing the position of the endotracheal tube, said first tube engaging strap defining a proximal end secured to said first foundation strap and an inner surface, at least a portion of which is coated with an adhesive for releasably engaging the endotracheal tube, said first tube engaging apparatus including a further tube engaging strap disposed between said first foundation strap and said first tube engaging strap, said further tube engaging strap of said first tube engaging apparatus defining a proximal end secured to said first foundation strap and defining an outer adhesive-coated surface for engaging the endotracheal tube; and a second tube engaging apparatus adapted for releasably engaging an endotracheal tube, said second tube engaging apparatus including a second foundation strap having a distal end portion and a further outer bonding surface proximate said distal end portion of said second foundation strap, said second tube engaging apparatus having a second tube engaging strap for releasably securing the position of the endotracheal tube, said second tube engaging strap defining a proximal end secured to said second foundation strap and an inner surface, at least a portion of which is coated with an adhesive for releasably securing the position of said endotracheal tube, said second tube engaging apparatus including a further tube engaging strap disposed between said second foundation strap and said second tube engaging strap, said further tube engaging strap of said second tube engaging apparatus defining a proximal end secured to said second foundation strap and defining an outer adhesive-coated surface for securing the position of the endotracheal tube.

16. An endotracheal tube holding device for securing the position of an endotracheal tube, said tube holding device comprising:

a first tube engaging apparatus adapted for releasably engaging an endotracheal tube, said first tube engaging apparatus including a first foundation strap having a distal end portion and a proximal end portion, said first tube engaging apparatus having a first tube engaging strap for releasably engaging and securing the position of the endotracheal tube, said first tube engaging strap defining a proximal end secured to said distal end portion of said first foundation strap and an outer adhesive-coated surface portion for releasably engaging the endotracheal tube; and a second tube engaging apparatus adapted for releasably engaging an endotracheal tube, said second tube engaging apparatus including a second foundation strap having a distal end portion and a proximal end portion, said second tube engaging apparatus having a second tube engaging strap for releasably engaging and securing the position of the endotracheal tube, said first tube engaging strap defining a proximal end secured to said distal end portion of said first foundation strap and an outer adhesive-coated surface portion for releasably engaging the endotracheal tube.

17. A method for securing the position of an endotracheal tube proximate the point at which the tube enters the body of a patient, said method comprising the steps of:

placing a first foundation strap proximate an endotracheal tube proximate the point at which the endotracheal tube enters the body of the patient;

placing a second foundation strap proximate the endotracheal tube proximate the point at which the tube enters the body of the patient;

utilizing a first tube engaging strap having a proximal end secured to said first foundation strap and having an adhesive-coated surface portion for engaging the endotracheal tube, adhesively bonding the first tube engaging strap to the endotracheal tube; and utilizing a second tube engaging strap having a proximal end secured to said second foundation strap and having an adhesive-coated surface portion for engaging the endotracheal tube, adhesively bonding the second tube engaging strap to the endotracheal tube.

18. The method for securing the position of an endotracheal tube of claim 17 wherein said step of placing a second foundation strap proximate the endotracheal tube includes placing the second foundation strap in a selectively spaced position along the endotracheal tube from the first foundation strap.

19. The method for securing the position of an endotracheal tube of claim 17 wherein said step of placing a second foundation strap proximate the endotracheal tube includes placing the second foundation strap diagonally across the first foundation strap.

20. The method for securing the position of an endotracheal tube of claim 17 wherein said method comprises the further steps of:

securing a first adhesive member to a proximal end portion of the first foundation strap, the first adhesive member defining an adhesive-coated surface portion;

adhesively bonding the adhesive-coated surface portion of the first adhesive member to the patient;

securing a second adhesive member to a proximal end portion of the second foundation strap, the second adhesive member defining an adhesive-coated surface portion; and adhesively bonding the adhesive-coated surface portion of the second adhesive member to the patient.

* * * * *